United States Patent
Farrugia et al.

(10) Patent No.: US 8,978,643 B2
(45) Date of Patent: Mar. 17, 2015

(54) MODIFICATION OF SYMPATHETIC ACTIVATION AND/OR RESPIRATORY FUNCTION

(75) Inventors: Steven Farrugia, Bella Vista (AU); Klaus Schindhelm, Bella Vista (AU)

(73) Assignee: ResMed Limited, Bella Vista, New South Wales (AU)

( * ) Notice: Subject to any disclaimer, the term of this patent is extended or adjusted under 35 U.S.C. 154(b) by 424 days.

(21) Appl. No.: 13/501,700

(22) PCT Filed: Oct. 14, 2010

(86) PCT No.: PCT/AU2010/001354
§ 371 (c)(1),
(2), (4) Date: Apr. 12, 2012

(87) PCT Pub. No.: WO2011/044627
PCT Pub. Date: Apr. 21, 2011

(65) Prior Publication Data
US 2012/0199126 A1    Aug. 9, 2012

Related U.S. Application Data

(60) Provisional application No. 61/272,628, filed on Oct. 14, 2009.

(51) Int. Cl.
*A61M 16/00* (2006.01)
*A62B 7/00* (2006.01)
*F16K 31/02* (2006.01)
*A61B 5/00* (2006.01)
(Continued)

(52) U.S. Cl.
CPC .............. *A61M 16/00* (2013.01); *A61B 5/0002* (2013.01); *A61B 5/0816* (2013.01); *A61B 5/087* (2013.01); *A61B 5/145* (2013.01); *A61B 5/4818* (2013.01); *A61M 2205/18* (2013.01); *A61M 2230/42* (2013.01)
USPC ..................................................... 128/200.23

(58) Field of Classification Search
CPC ............ A61M 16/00; A61M 16/0051; A61M 2205/3331; A61M 2205/50; A61M 2230/005; A61M 2230/40; A61M 2230/42; A61B 5/4818; A61B 5/087; A61B 5/0816
USPC ............. 128/203.12, 203.14, 204.18, 204.21, 128/204.23
See application file for complete search history.

(56) References Cited

U.S. PATENT DOCUMENTS

2005/0061319 A1   3/2005   Hartley et al.
2006/0000475 A1*  1/2006   Matthews et al. ........ 128/204.21
(Continued)

FOREIGN PATENT DOCUMENTS

EP    1621130    2/2006
WO    99/61088   12/1999
(Continued)

OTHER PUBLICATIONS

International Search Report dated Feb. 8, 2011 for PCT/AU2010/001354.

*Primary Examiner* — Kristen Matter
(74) *Attorney, Agent, or Firm* — Jones Day

(57) ABSTRACT

Devices, systems and methods are disclosed for modifying sympathetic activation of a patient through alteration of respiratory function. In one form, a sub-apneic ventilation target for a ventilator is determined such that chronic sympathetic activation of the patient is mitigated.

66 Claims, 9 Drawing Sheets

(51) Int. Cl.
*A61B 5/08* (2006.01)
*A61B 5/087* (2006.01)
*A61B 5/145* (2006.01)

(56) References Cited

U.S. PATENT DOCUMENTS

2007/0056582 A1* 3/2007 Wood et al. .............. 128/200.24
2010/0108066 A1 5/2010 Martin et al.
2012/0085347 A1* 4/2012 Iyer et al. ................. 128/204.21
2012/0152252 A1* 6/2012 Matthews et al. ........ 128/204.23
2013/0333696 A1* 12/2013 Lee et al. ................. 128/200.24

FOREIGN PATENT DOCUMENTS

WO 02/47747 6/2002
WO 2008/058328 5/2008

* cited by examiner

MODIFICATION OF SYMPATHETIC ACTIVATION AND/OR RESPIRATORY FUNCTION

This application is the National Phase application of International Application No. PCT/AU2010/001354, filed Oct. 14, 2010, which designates the United States and was published in English, which claims priority to U.S. Provisional Application No. 61/272,628, filed Oct. 14, 2009. These applications, in their entirety, are incorporated herein by reference.

CROSS REFERENCE

The entire content of each of the following references is hereby incorporated by reference: International Publication Nos. WO03/008027; WO 98/12965; WO 99/61088; WO 2009/109013 and PCT/AU2009/000671 application, filed May 28, 2009 and PCT/EP2009/002532 application, filed Apr. 6, 2009; U.S. Pat. Nos. 6,484,719; 7,520,279; 5,630,413; 6,532,959 and 6,532,957; U.S. provisional application Ser. No. 61/045,161, filed on Apr. 15, 2008 and U.S. provisional application Ser. No. 61/045,161, filed Apr. 15, 2008; U.S. patent application Ser. No. 12/585,572, filed Sep. 17, 2009; Ser. No. 14/422,411, filed Apr. 13, 2009; Ser. No. 11/494,522, filed Jul. 28, 2006 and Ser. No. 11/491,016, filed Jul. 24, 2006.

FIELD

The present disclosure is related to devices, systems, processor-readable media, and methods for inhibiting, and/or reducing sympathetic activation through control, and/or alteration of respiratory function. The present disclosure is also related to devices, systems, processor-readable media, and methods for controlling, and/or altering the respiratory function of a patient.

BACKGROUND

The autonomic nervous system (ANS) is part of the peripheral nervous system; it controls the activities of organs, glands and various involuntary muscles such as cardiac and smooth muscle. The ANS helps the body to adapt to changes in the environment and respond to stress. The ANS helps regulate: the size of blood vessels and blood pressure; the heart's electrical activity and ability to contract; the bronchium's diameter and thus air flow in the lungs.

The ANS affects heart rate, respiration rate, thermal regulation, digestion, salivation, perspiration, diameter of the pupils, urinary and sexual functions, metabolic and endocrine physiology.

The ANS acts through a balance of its two components, the sympathetic nervous system and parasympathetic nervous system.

The sympathetic nervous system (SNS) is involved in the stimulation of activities that prepare the body for action, such as increasing the heart rate, increasing the release of sugar from the liver, constricting blood vessels in organs not essential to fight or flight and other activities considered as fight-or-flight response.

The parasympathetic nervous system (PNS) activates resting functions, such as stimulating the secretion of saliva or digestive enzymes into the stomach and small intestine.

Generally, both sympathetic and parasympathetic systems target the same organs, but often antagonistically, e.g., the sympathetic system accelerates heart rate, while the parasympathetic system slows heart rate. Ordinarily, each system is stimulated appropriately to maintain homeostasis.

Autonomic failure, occurs when there is an imbalance between the sympathetic and parasympathetic divisions. Due to the many systems over which the autonomic nervous system exerts control, autonomic imbalance has manifold effects on the body, having serious cardiovascular, metabolic and endocrine consequences.

In particular, chronic sympathetic nervous system activation (SNS over-activity), plays a role in hypertension, Type II diabetes, obesity, metabolic syndrome and congestive heart failure. In essential hypertension, chronic sympathetic activation has been demonstrated to enhance cardiac myocyte growth, contributing to the development of left ventricular hypertrophy. In Type 2 Diabetes, chronic sympathetic activation contributes to increased insulin resistance and glucose intolerance.

Chronic sympathetic activation plays a significant role in cardiovascular disease. There is emerging evidence of a direct, causal linkage to the incidence of coronary heart disease clinical endpoints, such as myocardial infarction and sudden death and contribution of chronic sympathetic activation to mortality in congestive heart failure.

Chronic sympathetic activation is associated with clinical depression. The risk of heart attack has also been shown to be high in patients with depressive illness.

Obstructive sleep apnea (OSA) is associated with hypertension, Type II diabetes, obesity, metabolic syndrome, cardiovascular consequences including congestive heart failure and other endocrine consequences.

OSA is primarily characterized by sleep fragmentation and intermittent hypoxemia. The physiological stress imposed by the hypoxia and sleep fragmentation lead to a number of consequences including the direct effects of hypoxia and oxidative stress, hypothalamic pituitary adrenal dysfunction, systemic inflammation, changes in adipokine levels, disruption of sleep architecture and chronic sympathetic activation. Sympathetic activation in OSA, is a mediator of the causal link to the co-morbidities. OSA is a chronic slowly progressive disease that often may go undiagnosed for many years. In addition, the sympathetic activation seen in OSA may be present long before the OSA presents as clinically significant.

Current approaches to reducing sympathetic activation include weight loss, dietary calorie restriction and exercise. These approaches are typically unreliable, as they require behavioral modification and compliance can be low. Alternatively drugs may be used, including drugs that promote weight loss, e.g., sibutramine and antihypertensive drugs (e.g., beta-adrenergic drugs). Drugs acting on the central nervous system to reduce sympathetic outflow can be effective treatments for hypertension, but generally act non-specifically due to the broad interaction of the SNS and can have a high frequency of central nervous side effects and are generally not well tolerated by patients in long term therapy.

There is a need in the art for devices, systems, processor-readable media, and methods for inhibiting and/or reducing sympathetic activation through control and/or alteration of respiratory function.

SUMMARY

In certain embodiments, the disclosure is directed to devices, systems, processor-readable media, and/or methods for modulating, inhibiting, and/or reducing sympathetic activation through control, and/or modulation of the respiratory function.

In certain embodiments, the disclosure is directed to devices, systems, processor-readable media, and/or methods for reducing, inhibiting, and/or modulating sympathetic activation through control, and/or modulation of breathing during sleep.

In certain embodiments, the disclosure is directed to devices, systems, processor-readable media, and/or methods for reducing, inhibiting, and/or modulating sympathetic activation through control and/or modulation of breathing, when the patient is awake, or combinations thereof.

Certain embodiments are directed to devices, systems, processor-readable media, and/or methods for alteration of respiratory function of a patient comprising the steps of: selecting a first ventilation target level and substantially applying that first ventilation target level to a patient; increasing the ventilation target level until the patient's average breath rate per minute is decreased to the desired level; and substantially maintaining the desired average breath rate per minute over a certain duration. In certain aspects, these methods are related to reducing sympathetic activation in a patient.

Certain embodiments are directed to devices, systems, processor-readable media, and/or methods for alteration of respiratory function of a patient comprising the steps of: selecting a first ventilation target level and substantially applying that first ventilation target level to a patient; decreasing the ventilation target level until the patient's average breath rate per minute is increased to the desired level; and substantially maintaining the desired average breath rate per minute over a certain duration. In certain aspects, these methods are related to reducing sympathetic activation in a patient.

Certain embodiments are directed to devices, systems, processor-readable media, and/or methods for reducing sympathetic activation through alteration of respiratory function of a patient comprising the steps of determining a patient's average breath rate per time period while the patient is sleeping and being ventilated at a first level; if needed applying an increased ventilation level to the patient until the patient's average breath rate per time period is substantially decreased to the desired level; and substantially maintaining the desired average breath rate per minute over a certain duration.

Certain embodiments are directed to devices, systems, processor-readable media, and/or methods for controlling and/or alteration the respiratory function of a patient comprising the steps of: selecting a first ventilation target level; substantially applying the first ventilation target level to a patient while the patient is sleeping, preparing to sleep, and/or relaxing; increasing the ventilation target level over a period of time until an apneic threshold is substantially reached; reducing the ventilation target level to a sub-apneic ventilation target; and substantially maintaining the sub-apneic ventilation target over a certain time period. In certain aspects, the devices, systems, processor-readable media, and/or methods are directed to reducing sympathetic activation.

Certain embodiments are directed to devices, systems, processor-readable media, and/or methods for reducing sympathetic activation through alteration of respiratory function of a patient comprising the steps of: selecting a first ventilation target level; substantially applying the first ventilation target level to a patient while the patient is sleeping, preparing to sleep, and/or relaxing; increasing the ventilation target level over a period of time until an apneic threshold is substantially reached; reducing the ventilation target level to a sub-apneic ventilation target; and substantially maintaining the sub-apneic ventilation target over a certain time period.

Certain embodiments are directed to devices, systems, processor-readable media, and/or methods for reducing sympathetic activation through alteration of respiratory function of a patient comprising the steps of: selecting a first ventilation target level; substantially applying the first ventilation target level to a patient while the patient is sleeping; decreasing the ventilation target level over a period of time until an apneic threshold is substantially reached; increasing the ventilation target level to a sub-apneic ventilation target; and substantially maintaining the sub-apneic ventilation target over a certain time period.

Certain embodiments are directed to methods for determining a sub-apneic ventilation target for a ventilator comprising the steps of: setting a ventilation target to an initial value; monitoring a patient's respiration for a duration; analyzing data representing the patient's respiration to detect events indicating an apneic threshold; if no events are detected, increasing the ventilation target and continue to monitor a patient's respiration for a duration; if events are detected, setting a sub-apneic threshold and reducing the ventilation target to substantially the sub-apneic threshold or lower; wherein the sub-apneic ventilation target is such that chronic sympathetic activation of the patient is mitigated when ventilation is provided at substantially the sub-apneic ventilation target.

Certain embodiments are directed to methods for determining a sub-apneic ventilation target for a ventilator comprising the steps of: setting a ventilation target to an initial value; setting a sub-apneic ventilation threshold to an initial value; monitoring a patient's respiration for a duration; analyzing data representing the patient's respiration to detect events indicating an apneic threshold; if no events are detected, increasing the ventilation target and confirm that the ventilation target is less then the sub-apneic threshold and continue to monitor a patient's respiration for a duration; if events are detected, updating the sub-apneic threshold and reducing the ventilation target substantially to the updated sub-apneic ventilation target or lower; wherein the sub-apneic ventilation target is such that chronic sympathetic activation of the patient is mitigated when ventilation is provided at the sub-apneic ventilation target.

Certain embodiments are directed to processor-readable medium having instructions therein that, when executed, cause a processor to perform the steps of: setting a ventilation target to an initial value; monitoring a patient's respiration for a duration; analyzing data representing the patient's respiration to detect events indicating an apneic threshold; if no events are detected, increasing the ventilation target and continuing to monitor the patient's respiration; if events are detected, setting a sub-apneic threshold and reducing the ventilation target to substantially the sub-apneic threshold or lower; wherein the sub-apneic ventilation target is such that chronic sympathetic activation of the patient is mitigated when ventilation is provided at substantially the sub-apneic ventilation target.

Certain embodiments are directed to devices for determining a sub-apneic ventilation target for a ventilator comprising: a blower in air communication with a mask worn by a patient; a respiratory monitor; a processor in communication with the respiratory monitor and the blower, wherein the processor controls the operation of the blower; and a memory connected to the processor, wherein the memory has instructions therein that cause the processor to perform the steps of, setting a ventilation target to an initial value; monitoring a patient's respiration for a duration; analyzing data representing the patient's respiration to detect events indicating an apneic threshold; if no events are detected, increasing the ventilation target; if events are detected, setting a sub-apneic threshold and reducing the ventilation target to substantially the sub-apneic threshold or lower; wherein the sub-apneic ventilation target is such that chronic sympathetic activation of the patient is mitigated when ventilation is provided at the sub-apneic ventilation target.

Certain embodiments are directed to devices, systems, processor-readable media, and/or methods of treating a patient with a chronic sympathetic activation disorder using a ventilator device, the ventilator device being attached to a patient interface device adapted to be attached to supply ventilation support to the patients airways, providing a level of ventilation support at a sub-apneic pressure level to the patient for a duration of time, wherein the sub-apneic threshold level prevents, or substantially prevents, the occurrence of central apneas and reduces sympathetic activation.

Certain embodiments are directed to devices, systems, processor-readable media, and/or methods of treating a patient with a chronic sympathetic activation disorder using a ventilator device, the ventilator device being attached to a patient interface device adapted to be attached to supply ventilation support to the patients airways, providing a level of ventilation support at a sub-apneic pressure level to the patient for a duration of time, wherein the sub-apneic threshold level prevents, or substantially prevents, the occurrence of central apneas, central hypopneas, flow limitations, or combinations thereof and reduces sympathetic activation.

Certain embodiments are directed to devices, systems, processor-readable media, and/or methods of treating a patient using a ventilator device, the ventilator device being attached to a patient interface device adapted to be attached to supply ventilation support to the patients airways, providing a level of ventilation support at a sub-apneic pressure level to the patient for a duration of time, wherein the treatment results in at least one or more of the following benefits: reduced sympathetic activation; increased parasympathetic activation; improved autonomic balance; reduced breath rate during sleep; reduced heart rate during sleep; and/or improved respiratory-cardiovascular coupling.

Certain embodiments are directed to devices, systems, processor-readable media, and/or methods of treating a patient using a ventilator device, the ventilator device being attached to a patient interface device adapted to be attached to supply ventilation support to the patients airways, providing a level of ventilation support at a sub-apneic pressure level to the patient for a duration of time, wherein the treatment results in at least one or more of the following: improved cardiovascular, endocrine, and/or metabolic outcomes in a range of disorders including, hypertension, Type 2 diabetes, obstructive sleep apnea, and/or metabolic syndrome.

The disclosed devices, systems, processor-readable media, and/or methods are for the modification, and/or inhibition of sympathetic activation and/or for controlling, and/or altering the respiratory function of a patient. The disclosed inventions offer at least one or more of the following benefits: reduced sympathetic activation; increased parasympathetic activation; improved autonomic balance; reduced breath rate during sleep; reduced heart rate during sleep; and/or improved respiratory-cardiovascular coupling. These benefits in turn lead to at least one or more improved cardiovascular, endocrine, and/or metabolic outcomes in a range of disorders including, but not limited to, hypertension, Type 2 diabetes, obstructive sleep apnea, and/or metabolic syndrome.

It is to be understood that many of these embodiments may be used with patients with or without OSA.

Various aspects of the described example embodiments may be combined with aspects of certain other example embodiments to realize yet further embodiments.

Other features of the technology will be apparent from consideration of the information contained in the following detailed description, abstract and claims.

BRIEF DESCRIPTION OF THE DRAWINGS

These and other features, aspects, and advantages of the present disclosure will become better understood with regard to the following description, appended claims, and accompanying drawings wherein:

DETAILED DESCRIPTION

Figure 1:
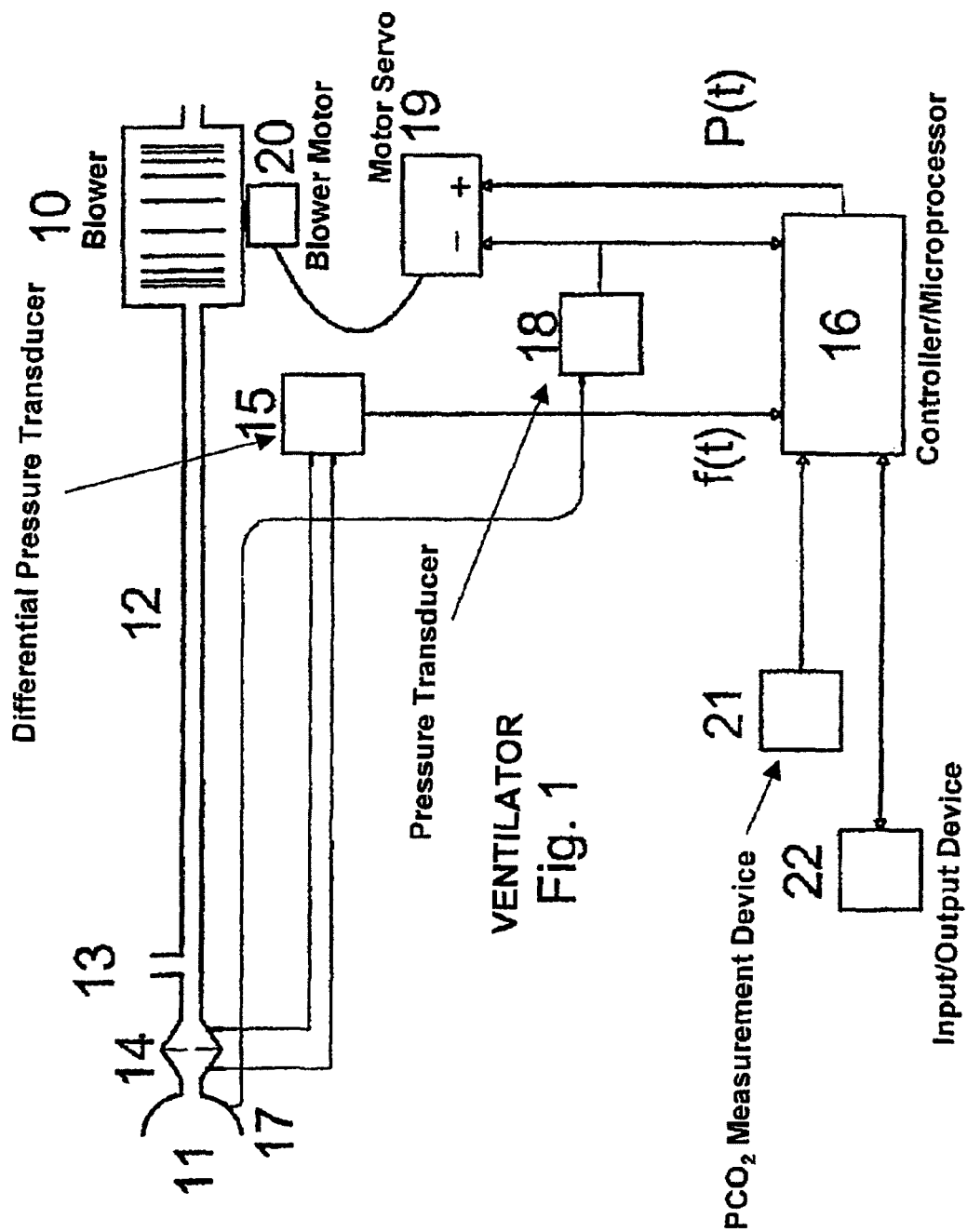
FIG. 1 shows an exemplary ventilator apparatus in accordance with certain embodiments.

Implementations of the present disclosure may be based on the use of a suitable positive airway pressure (PAP) device. For example, a bilevel device, e.g., an AutoVPAP device, a VPAP III, a CPAP, a bilevel variant of an OpenCPAP device, or other non-invasive ventilation devices. As used herein non-invasive ventilation (NIV) refers to the delivery of mechanical ventilation using a face mask or nasal prongs or similar patient interface. In certain NIV device configurations, at least two levels of pressure support are provided: a higher inspiratory positive airway pressure (IPAP) and a lower expiratory positive airway pressure (EPAP). The NIV devices used in this disclosure may incorporate multiple modes. For example, in the S Mode (or spontaneous mode) the device triggers to IPAP when a spontaneous inspiratory effort is detected and then cycles back to EPAP when exhalation is detected. In the T Mode (or timed mode), the IPAP/EPAP cycling is machine-triggered, at a set rate. In the S/T Mode, the device triggers to IPAP on patient inspiratory effort, but a "backup" rate is also set to ensure that the patient receives a minimum number of breaths per minute if they fail to breathe spontaneously.

The effects of NIV on a patient's respiration include: augmented volume and/or high inspiratory flow-rates due to afferent feedback via mechanoreceptors; suppressed respiratory drive, due to improved blood gases; reduced work of breathing, due to improved blood gases, allowing a reduced respiratory drive; increased total breath duration with increasing pressure-support due primarily to increased duration of exhalation or combinations thereof.

Certain embodiments of the disclosed devices, systems, processor-readable media, and/or methods are directed to the modification, and/or inhibition of sympathetic activation. Many of these embodiments may be used with patients with or with out OSA.

Certain embodiments, of the disclosed devices, systems, processor-readable media, and/or methods are directed to controlling and/or altering the respiratory function of a patient. Again, many of these embodiment may be used with patients with or without OSA.

Certain embodiments of the present disclosure offer at least one or more of the following benefits: reduced sympathetic activation; increased parasympathetic activation; improved autonomic balance; reduced breath rate during sleep; reduced heart rate during sleep; and/or improved respiratory-cardiovascular coupling. These benefits in turn lead to at least one or more improved cardiovascular, endocrine, and/or metabolic outcomes in a range of disorders including, but not limited to, hypertension, Type 2 diabetes, obstructive sleep apnea and/or metabolic syndrome.

Many of the disclosed embodiments may be used with patients with or without OSA. For example, to treat hypertensive or diabetic patients or patients with other metabolic disorders.

Certain embodiments, may be combined with other methodologies in order to provide a combined treatment for OSA and the other diseases discussed herein. Certain embodiments may be used to treat OSA and the other diseases discussed herein.

Certain embodiments of the present disclosure offer at least one or more of the following benefits: reduced sympathetic activation; increased parasympathetic activation; improved autonomic balance; reduced breath rate during sleep; reduced heart rate during sleep; and/or improved respiratory-cardiovascular coupling in patients that do not have OSA. These benefits in turn lead to at least one or more improved cardiovascular, endocrine and/or metabolic outcomes in a range of disorders including, but not limited to, hypertension, Type 2 diabetes, and/or metabolic syndrome in patients that do not have OSA.

Certain embodiments of the present disclosure are directed to devices, systems, processor-readable media, and methods of determining ventilation target, and thereby reducing, inhibiting, and/or modulating sympathetic activation via control, and/or modulation of breathing.

Certain embodiments of the present disclosure are directed to devices, systems, processor-readable media, and methods of determining, and/or setting at least one ventilation target, and thereby reducing, inhibiting, and/or modulating sympathetic activation via control and/or modulation of breathing.

Certain embodiments of the present disclosure are directed to devices, systems, processor-readable media, and methods of determining a sub-apneic ventilation target, and thereby reducing, inhibiting, and/or modulating sympathetic activation via control, and/or modulation of breathing.

In certain aspects, the devices, systems, processor-readable media, and/or methods may be used while the patient is sleeping. In certain aspects, the devices, systems, processor-readable media, and methods may be used while the patient is awake and relaxed. In certain aspects, the patient may be asleep, awake, or combinations thereof.

In certain embodiments, an initial ventilation target will be set or determined. This can be done by a number of means. For example, it may be: a nominal physiological value; a value calculated using a formula, e.g., based on the patient's height; a value determined from a table; set to the patient's eupneic ventilation at the start of therapy, determined by measurement or a function thereof or a stored value from a previous treatment session or a function thereof; or combinations thereof.

In certain embodiments the sub-apneic level ($V_{SUB-APNEIC\ THRESHOLD}$) will be set or determined. This may be done at the beginning of the process and/or at some later stage in the process. This may also be maintained at a set point, adjusted at certain time intervals, semi-continuously adjusted up or down as needed, continuously adjusted up or down as needed, or combinations thereof. Typically, for certain embodiments, this will be set or determined in relationship to the physiological apneic threshold.

In certain embodiments, the sub-apneic level may be set at a pre-selected level based on what is believed to be near the physiological apneic threshold based on information, and/or data that has been previously collected about the patient, general information about where the apneic physiological threshold is typically found, other acceptable means, or combinations thereof.

In certain embodiments, the sub-apneic level may be set or determined based on a nominal physiological value; a value calculated using a formula, e.g., based on the patient's height; a value determined from a table; determined by measurement or a function thereof or a stored value from a previous treatment session or a function thereof. PCO2 measurements, or combinations thereof. In certain embodiments, the sub-apneic level may be set or determined based on a ratio, percentage, or some other relationship between the sub-apneic level and the physiological apneic threshold.

In certain embodiments, the aim is to set the sub-apneic level so that it is reasonably close to the physiological apneic level but sufficiently distance from the physiological apneic level so as to minimize, or substantially minimize, the occurrences of apneas once treatment has commenced.

In certain embodiments, it may be expected that the physiological apneic threshold may move up or down during different sleep stages, with disease progression, due to medication, or other reasons. Accordingly, the sub-apneic level ($V_{SUB-APNEIC\ THRESHOLD}$) may also need to increase, and/or decrease as needed.

In certain embodiments, the sub-apneic ventilation threshold is set to the physiological apneic threshold, minus a small margin (or buffer). The value of the margin may be set in a number of ways; for instance it may be a predetermined fixed value or it could be calculated as a percentage of the current ventilation target. For example, the margin may be about 1%, about 2%, about 3%, about 4%, about 5%, about 6%, about 7%, about 8%, about 9% or about 10% of the ventilation target. In certain embodiments, margin can be a value less than the difference between the patient's ventilation at the apneic threshold and their eupneic ventilation value calculated or determined at the beginning of the session. In certain embodiments, the margin may be omitted. The desire is provide treatment level of ventilation support at a sub-apneic pressure level to the patient for a duration of time, wherein the sub-apneic threshold level prevents, or substantially prevents, the occurrence of central apneas, central hypopneas, flow limitations, or combinations thereof.

In certain embodiments, the implementation may be based on the AutoVPAP device and may be implemented either as a manual process, or may be automated as an algorithm implemented on the AutoVPAP. The implementation may also be carried out by combining certain manual processes with certain automated processes.

In certain embodiments, a sleep stage monitor, and/or alarm may be incorporated into the disclosure devices, systems, processor-readable media, and methods. This sleep stage monitor, and/or alarm may be used to assist with monitoring, and/or setting ventilation levels, and/or sub-apneic threshold. This may be useful since many of the embodiments are directed to determining, and/or treating a patient near the physiological apneic threshold. Since central apneas, central hypopneas, flow limitations, or combinations thereof may occur it may be useful to incorporate some type of sleep monitor, and/or alarm as an additional safety measure or control.

In certain embodiments, a monitor and/or alarm may be incorporated into the flow generator, patient interface, headgear, or combinations thereof. See for example, U.S. patent application Ser. No. 11/491,016. This type of monitor, and/or alarm may be adapted to function as an appropriate monitor and/or alarm for use herein. The sleep stage monitor may be structured to monitor a person's sleeping pattern and clearly identify the NREM and REM sleep cycles and the durations of each cycle and provide the desired safety thresholds with respect to events detected such as central apneas, central hypopneas, flow limitations or combinations during different stages of sleep. Monitoring may be done by detecting eye movement or by receiving signals from electrodes attached to parts of a person's body. Eye movement may be detected by eye sensors that may be worn on the person's forehead like spectacles or headbands. Also, the eye sensors may be incorporated into the patient interface, and/or headgear arrangement. The electrodes, e.g., body or face electrodes, may be in the form of a patch with small suction pads so it attaches to the person's skin. Signals from the sensors may be detected, enhanced, and amplified by a detector before they are communicated to the central processor.

The central processor may evaluated the signals and determine the part of the sleep cycle the person is at, the quality of the sleep, and/or the number of sleep cycles completed. Also, the central processor may gather and analyze information from other inputs, such as, but not limited to, the blood $O_2$ and the $CO_2$ levels and this information may used alone or in combination with other events to adjust the amount of ventilation, and/or set off an alarm.

The selected sleep pattern may be controlled by a software program that is based on stored medical data in the monitor or in a computer. Thus, the information may be updated to enhance the programs. The central processor may have a large memory to record the sleeping patterns and other information. The recorded information may be used by a clinician to study the patients sleeping pattern, ventilation pattern, and/or to enhance the treatment. Also, the monitor/alarm may be connected to a network and be monitored remotely.

An exemplary servo-controlled ventilator is shown in FIG. 1. A blower 10 supplies air under pressure via delivery tube 12 to a mask 11 or nasal prongs via another such patient interface device for providing flow to a patient's respiratory system. Exhaust gas is vented via exhaust 13. Mask flow may be measured using pneumotachograph 14 and differential pressure transducer 15 to derive flow signal f(t). In some applications, not shown the pneumotach may be located within the flow generator. Mask pressure is measured at pressure tap 17 using pressure transducer 18. Flow and pressure signals are sent to a controller or microprocessor 16 including a memory which implements the processing described herein to derive a pressure request signal P(t). Programmed instructions accessible to the microprocessor may be coded on integrated chips in the memory of the device or may be loaded as software and stored by some other data storage medium of conventional design (not shown). The actual measured pressure and pressure request signal P(t) are fed to motor servo 19 which controls blower motor 20 to produce the desired instantaneous mask pressure. In certain embodiments, an automated PCO2 measurement device 21 or other non-invasive blood gas monitor/device for measuring PCO2 may be linked to provide an input data signal to the microprocessor 16, for example, a device as taught in U.S. Pat. No. 5,630,413. Optional input, and/or output devices 22 may be included to display output signals and enter input signals for the microprocessor 16. Various appropriate input and output devices such as keypads and display screens and other alternatives can be included. An example of this type of servo-controlled ventilator is the subject of International Publication No. WO 98/12965, which is also disclosed in related U.S. Pat. No. 6,532,957. Additional examples are disclosed in International Publication No. WO 99/61088, which is also contained in related U.S. Pat. No. 6,532,959 and in International Publication No. WO03/008027, which is also contained in U.S. Pat. No. 7,520,279.

Figure 9:
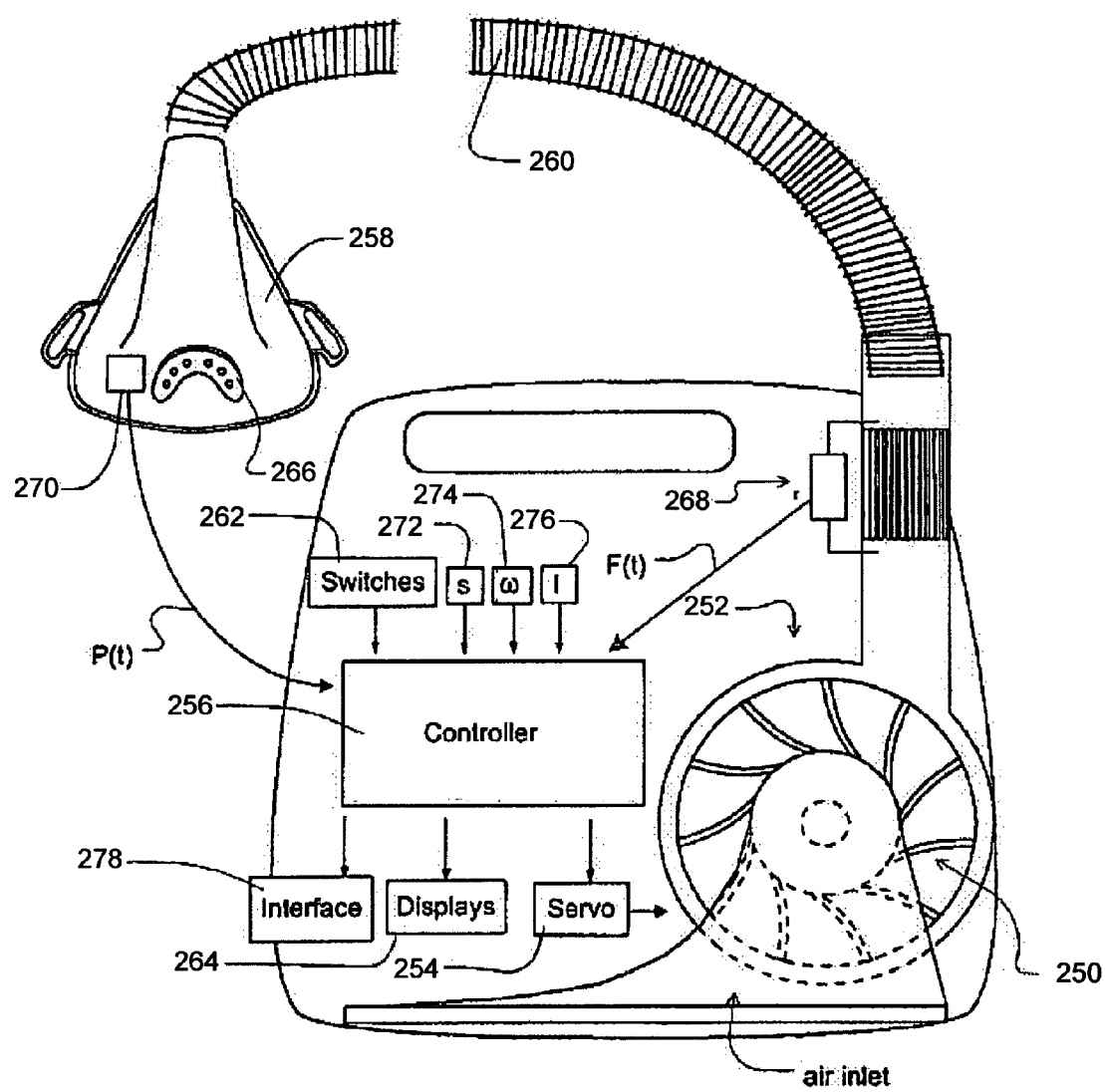
FIG. 9 shows an exemplary apparatus according to certain embodiments.

FIG. 9 shows another exemplary apparatus suitable for performing certain disclosed embodiments. The apparatus includes an impeller 250 connected to an electric motor 252 under the control of a servo-controller 254 which is in turn under the control of a controller 256. In one form the controller 256 is a micro-processor based controller. The impeller 250 and motor 252 form a blower. Air from the blower passes along a flexible conduit 260 to a patient interface such as a nasal mask 258 with a vent 266. While a nasal mask is illustrated, certain disclosed embodiments may be used in conjunction with a nose-and-mouth mask, full face mask, nasal prongs or other devices that perform the desired function. A number of switches 262 are connected to the controller. A number of sensors are also connected to the controller, for example, sensors for flow 268, pressure 270, snore 272, motor speed 274 and motor current 276. A set of displays 264 connected to the controller 256 display information from the controller.

An interface 278 enables the controller 256 to communicate with an external device such as a computer. With such a device, changes in the speed of the blower may be controlled to alternatively change the pressure in the mask to implement ventilatory support. Optionally, the blower motor speed may be held generally constant and pressure changes in the mask may be implemented by controlling an opening of a servo-valve (not shown) that may variably divert/vent or deliver airflow to the mask. Those skilled in the art will recognize other devices for generating ventilatory support and delivering same to a patient.

The controller 256 or processor may be configured and adapted to implement certain of the methodologies described herein and may include integrated chips, a memory and/or other instruction or data storage media. For example, programmed instructions with the control methodology may be coded on integrated chips in the memory of the device or such instructions may be loaded as software. With such a controller, the apparatus can be used for many different pressure ventilation therapies simply by adjusting the pressure delivery equation that is used to set the speed of the blower or to manipulate the venting with the release valve. Those skilled in the art will also recognize that aspects of the controller may also be implemented by analog devices or other electrical circuits.

The apparatus can further include a communication module, for example, a wireless communication transceiver, and/or a network card, for communication with other devices or computers such as hand-held display and control devices. The apparatus optionally includes an oximeter in the main blower housing. A sense tube may be connected to the main housing of the blower or the mask to allow the apparatus to sense oxygen concentration and pressure levels in the mask. The apparatus may further include additional diagnosis units such as a pulse oximeter and respiratory movement sensors. The unit may also include a set of electrodes for detecting cardiac rhythm.

It is understood that a combination of devices, and/or computers linked by available communications methods may be used to accomplish the desired goals. For example, the apparatus can interface with a variety of hand-held devices such as a Palm Pilot via wireless communication. With such a device, a physician may, for example, remotely monitor, analyze or record the status or data history of a patient or diagnose the severity of the patient's condition using the device. Furthermore, the treatment program that is being run on the patient can be monitored and changed remotely.

For exemplary purposes, the operation of certain exemplary embodiments will be described with reference to the components of FIG. 1. However, the exemplary operations described are also applicable to other embodiments of the present disclosure including the exemplary apparatus of FIG. 9. In operation, a patient dons a mask attached to a ventilator in accordance with the present disclosure. The servo-controlled blower 10 is then controlled by, for example, controller or microprocessor 16, to provide PAP at a ventilation target level. This ventilation target level may also be set manually if desired in certain applications.

Figure 2:
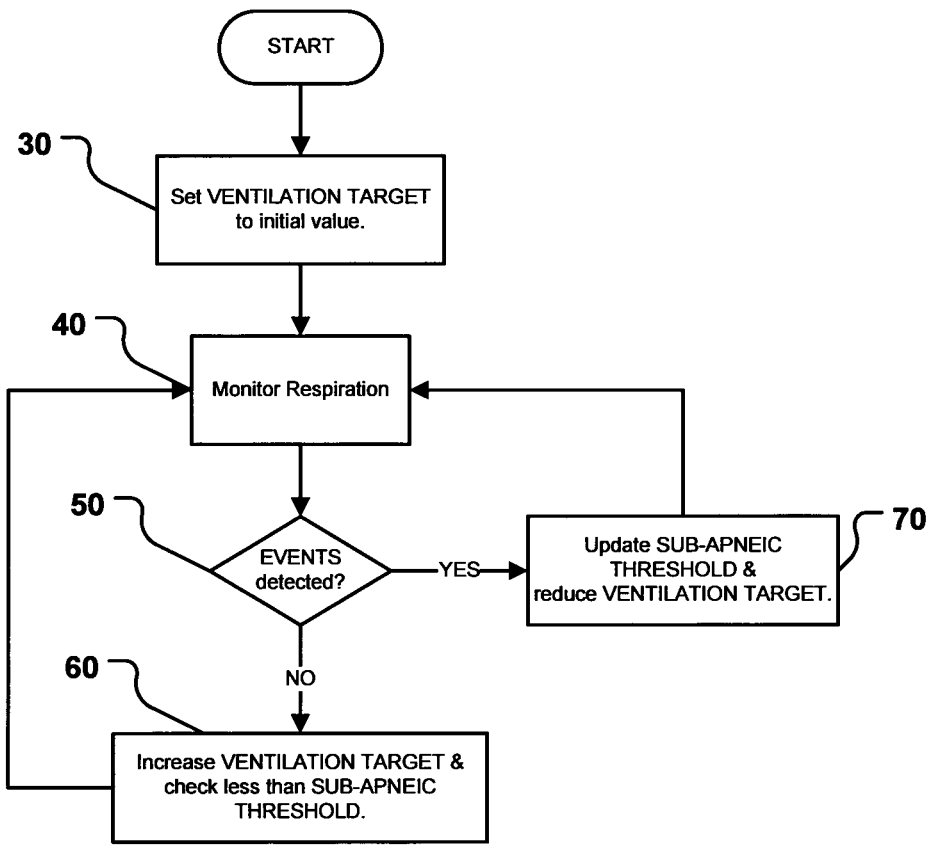
FIG. 2 illustrates an exemplary technique in accordance with certain embodiments.

A ventilation target may be adjusted, for example, on a continuous basis using a control algorithm. In alternative embodiments, the therapy may be divided into distinct titration and treatment periods, in which case the control algorithm can be applied during the titration phase to determine the ventilation target and then the ventilation target may be set to a fixed value for subsequent therapy during the treatment phase. An exemplary control algorithm executed by the controller or microprocessor 16 operates as illustrated in FIG. 2.

In step 30, the controller or microprocessor 16 sets an initial value for the ventilation target ($V_{TARGET}$). The initial ventilation target may be determined in a number of ways. For example, it may be: a nominal physiological value; a value calculated using a formula, e.g. based on the patient's height; a value determined from a table; set to the patient's actual ventilation, determined by measurement or a function thereof; or a stored value from a previous treatment session or a function thereof; or any suitable combination of any of these techniques. In addition, optionally in step 30, the controller or microprocessor 16 sets an initial a sub-apneic ventilation threshold ($V_{SUB-APNEIC\ THRESHOLD}$). The initial value of the sub-apneic ventilation threshold may be determined in a number of ways. For example, it may be: a nominal physiological value; a value calculated using a formula, e.g. based on the patient's height; a value determined from a table; a function of the patients eupneic ventilation, determined by measurement of the patients ventilation at the beginning of the session or a function thereof; or a stored value from a previous treatment session or a function thereof; or a suitable combination of these techniques. In certain embodiments, the initial value for the ventilation target ($V_{TARGET}$) and the initial sub-apneic ventilation threshold ($V_{SUB-APNEIC\ THRESHOLD}$) do not have to be set at the same time. They may be in set in sequence as well.

In step 40, respiration is monitored for some duration. For example, the mask flow may be measured using pneumotachograph 14 and differential pressure transducer 15 to derive flow signal f(t). A suitable duration might be, for example, about 5 minutes, about 10 minutes, about 20 minutes, about 30 minutes or about 40 minutes but shorter or longer durations may be used.

During the monitoring duration, the controller or microprocessor 16 analyzes data to detect events. Events may be measured, for example, as the apnea hyponea index (AHI), the hypopnea index (HI), the apnea index (AI), or combinations thereof. Methods for apnea and hypopnea detection are well established and known to those familiar with the art. In step 50 if no events are detected within the monitored interval, or the number of events is less than some predetermined value (e.g., AHI<4, <5, <6, <7 or <8), then the process proceeds to step 60. In another embodiment, events may be defined in terms of the ventilator mode, such that a switch to "timed mode" is considered an event.

In step 60, the controller or microprocessor 16 sets a new ventilation target that is greater than the current value of the ventilation target, and the process returns to step 40. The new ventilation target may be set in a single step, or increased incrementally over a number of breaths or period of time, so as to avoid causing arousal due to sudden changes in ventilation or pressure support levels. Additionally, if no events have been detected for a number of iterations, the sub-apneic ventilation threshold value is also increased. In certain embodiments, the physiological apneic threshold may move up or down during different sleep stages, with disease progression, due to medication, or other reasons. In these situations a mechanism is needed for $V_{SUB-APNEIC\ THRESHOLD}$ to also increase, and/or decrease. Typically, this will occur slowly and often over only after a number of iterations with no events.

The new ventilation target is also compared to the sub-apneic ventilation threshold value, to ensure that it is less than the sub-apneic ventilation threshold value.

If the new ventilation target is greater than the sub-apneic threshold ventilation value, then the ventilation target is set equal to the sub-apneic ventilation threshold value.

Referring back to step 50, if events are detected within the monitored interval, then the control algorithm proceeds to step 70.

In step 70, the sub-apneic ventilation threshold is set to the current ventilation target, minus a small margin (or buffer) and a new ventilation target is set, less than the current ventilation target, and the process returns to step 40. The value of the margin may be set in a number of ways; for instance it may be a predetermined fixed value or it could be calculated as a percentage of the current ventilation target. For example, the margin may be about 1%, about 2%, about 3%, about 4%, about 5%, about 6%, about 7%, about 8%, about 9% or about 10% of the current ventilation target. In certain embodiments, the amount by which the target ventilation is reduced (decremented) can be different to the value of the margin.

In addition, as the patient's respiration approaches, or substantially approaches, the physiological apneic threshold, the respiration of the patient may be somewhat ventilator dependent; so suddenly removing pressure support or suddenly dropping the level of support, may result in apnea. Accordingly, in certain embodiments, it may be desirable to slowly, or more slowly, modify the ventilation support as the patient approaches the physiological apneic.

Similarly to step 60, the new ventilation target may be set in a single step, or decreased incrementally over a number of breaths or period of time to its final value.

The sub-apneic threshold is used in step 60 to ensure that the ventilation target is not set to a value greater than the physiological apneic threshold, which may result in apnea and oscillation of the target ventilation. Typically, the sub-apneic threshold includes a margin to further mitigate the chance of oscillation, although this margin may be omitted in certain embodiments. The exemplary control algorithm illustrated in FIG. 2, may be used with patients with or without OSA.

Figure 3:
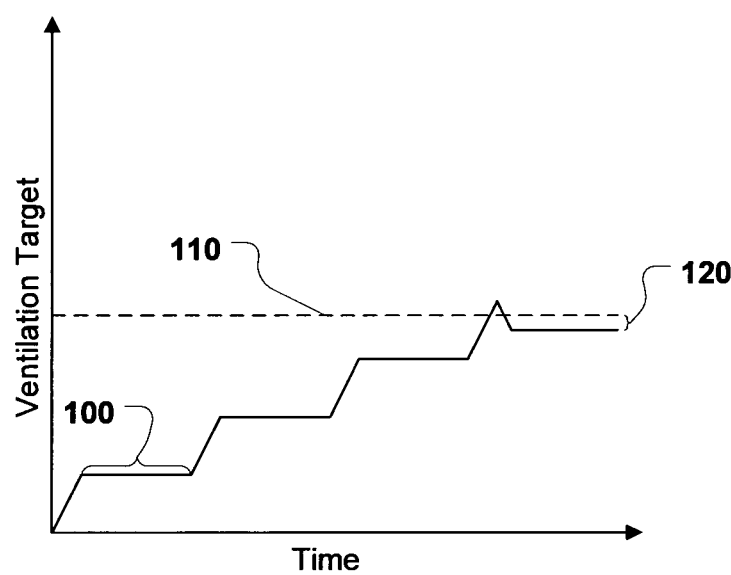
FIG. 3 illustrates an exemplary graph showing the ventilation target vs. time in accordance with certain embodiments.

FIG. 3 shows an exemplary graph illustrating how the ventilation target converges toward the apneic threshold over time in accordance with certain embodiments. As shown in FIG. 3, the ventilation target is increased and then held relatively constant for a monitoring duration 100. The ventilation target is then increased and held again repeatedly until events are detected. The occurrence of the events indicates that the apneic threshold 110 has been crossed. At this point, the ventilation target is set at a value below the apneic threshold 110 by a margin 120.

Figure 4:
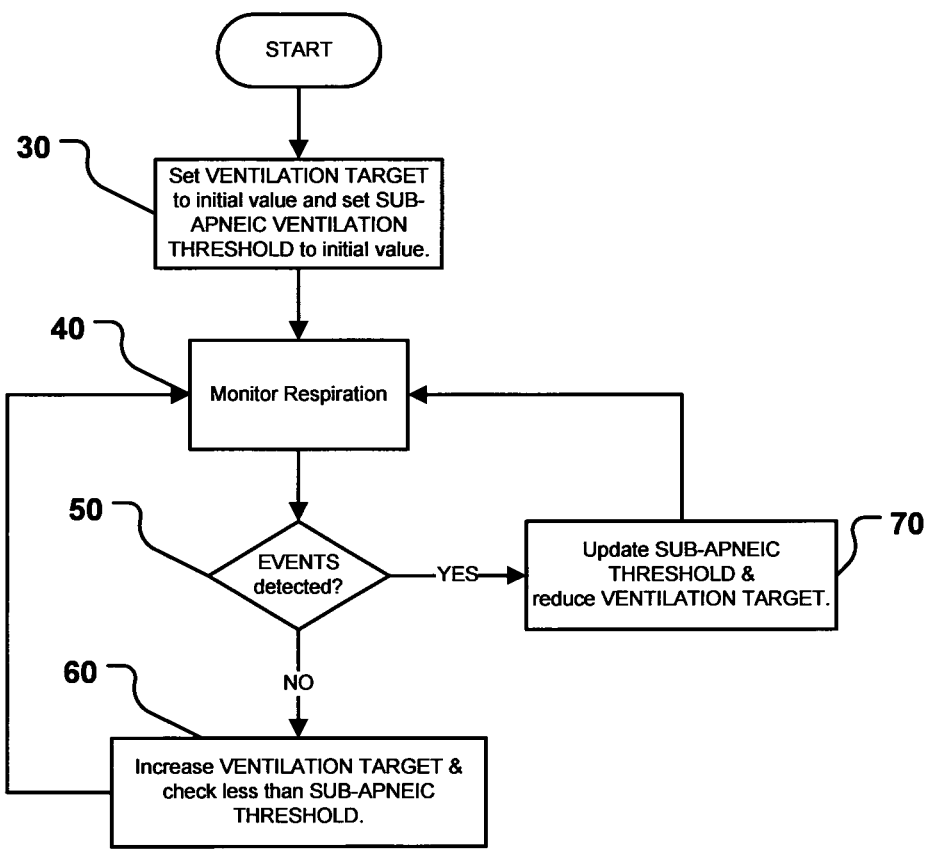
FIG. 4 illustrates an exemplary technique in accordance with certain embodiments.

An exemplary control algorithm is illustrated in FIG. 4. In step 30 the controller or microprocessor 16 sets an initial value for the ventilation target ($V_{TARGET}$). In addition, in step 30, the controller or microprocessor 16 sets an initial a sub-apneic ventilation threshold ($V_{SUB-APNEIC\ THRESHOLD}$). Otherwise the process is similar to that shown in FIG. 2.

Figure 5:
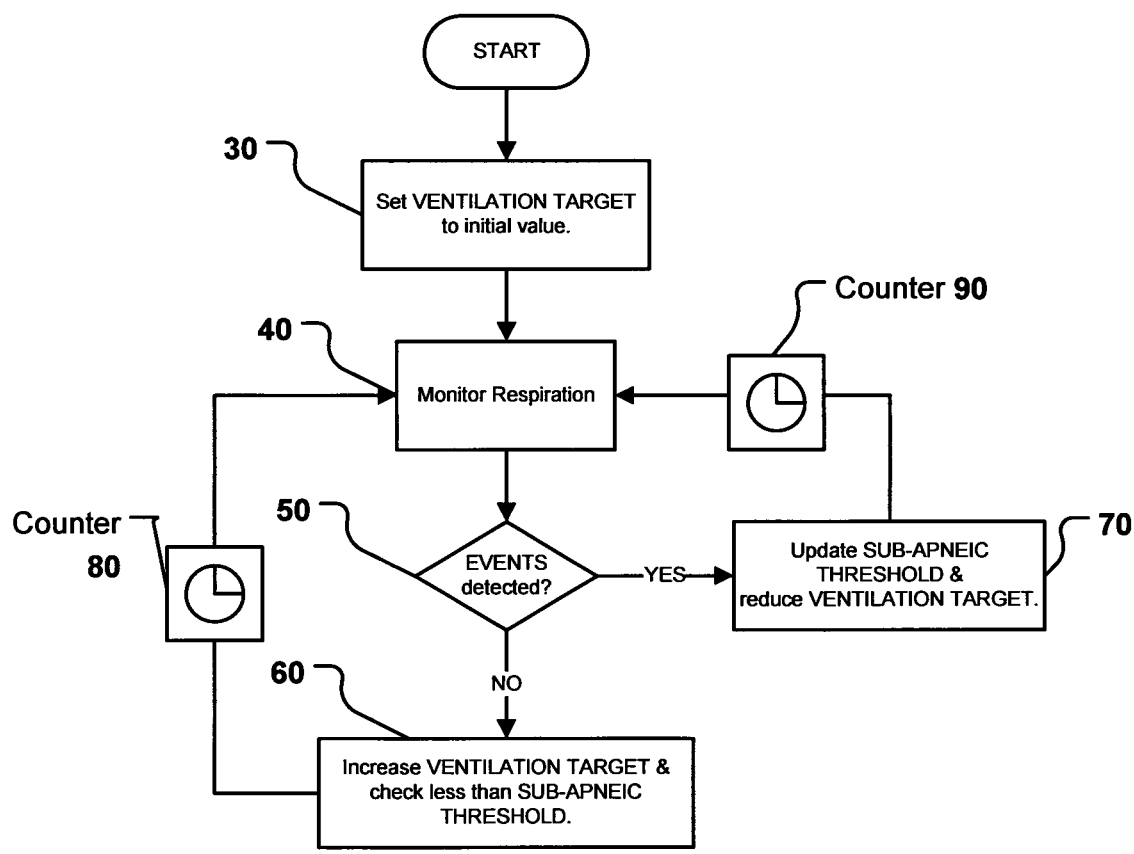
FIG. 5 illustrates an exemplary technique in accordance with certain embodiments.

An exemplary control algorithm is illustrated in FIG. 5. Here in step 30, the controller or microprocessor 16 sets an initial value for the ventilation target ($V_{TARGET}$). The initial ventilation target may be determined in a number of ways as discussed herein.

In step 40, respiration is monitored for some duration. A suitable duration might be, for example, about 5 minutes, about 10 minutes, about 20 minutes, about 30 minutes or about 40 minutes but shorter or longer durations may be used.

During the monitoring duration, the controller or microprocessor 16 analyzes data to detect events. Events may be measured, for example, as the apnea hyponea index (AHI), the hypopnea index (HI), the apnea index (AI), or combinations thereof. Methods for apnea and hypopnea detection are well established and known to those familiar with the art. In step 50 if no events are detected within the monitored interval, or the number of events is less than some predetermined value (e.g., AHI<4, <5, <6, <7 or <8), then the process proceeds to step 60.

In step 60, the controller or microprocessor 16 sets a new ventilation target that is greater than the current value of the ventilation target, and the process returns to step 40. The new ventilation target may be set in a single step, or increased incrementally over a number of breaths or period of time, so as to avoid causing arousal due to sudden changes in ventilation or pressure support levels. Additionally, if no events have been detected for a number of iterations, the sub-apneic ventilation threshold value is also increased. In certain embodiments, the physiological apneic threshold may move up or down during different sleep stages, with disease progression, due to medication, or other reasons. In these situations a mechanism is needed for $V_{SUB-APNEIC\ THRESHOLD}$ to also increase and/or decrease. Typically, this will occur slowly and often over only after a number of iterations with no events. This may be implemented by adding between step 60 and 40 some type of loop counter 80, or other mechanism, that will increase the ventilation target after certain number of loops, for example 3. Other acceptable numbers of loops may be 0, 1, 2, 3, 4, 5, 6, 7, 8, 9 or more.

The new ventilation target is also compared to the sub-apneic ventilation threshold value, to ensure that it is less than the sub-apneic ventilation threshold value.

If the new ventilation target is greater than the sub-apneic threshold ventilation value, then the ventilation target is set equal to the sub-apneic ventilation threshold value.

Referring back to step 50, if events are detected within the monitored interval, then the control algorithm proceeds to step 70.

In step 70, the sub-apneic ventilation threshold is set to the current ventilation target, minus a small margin (or buffer) and a new ventilation target is set, less than the current ventilation target, and the process returns to step 40. In addition, the loop counter 90 resets the loop counter to zero. The value of the margin may be set in a number of ways as disclosed herein. Similarly to step 60, the new ventilation target may be set in a single step, or decreased incrementally over a number of breaths or period of time to its final value.

The sub-apneic threshold is used in step 60 to ensure that the ventilation target is not set to a value greater than the physiological apneic threshold. In certain embodiments, storage of the apneic threshold could be omitted, but this may lead to oscillation of the ventilation target, as it crosses the physiological apneic threshold and is reset. Typically, the apneic threshold also includes a margin to further mitigate the chance of oscillation, although this margin may be omitted in certain embodiments. The exemplary control algorithm illustrated in FIG. 4 may be used with patients with or without OSA.

Figure 6:
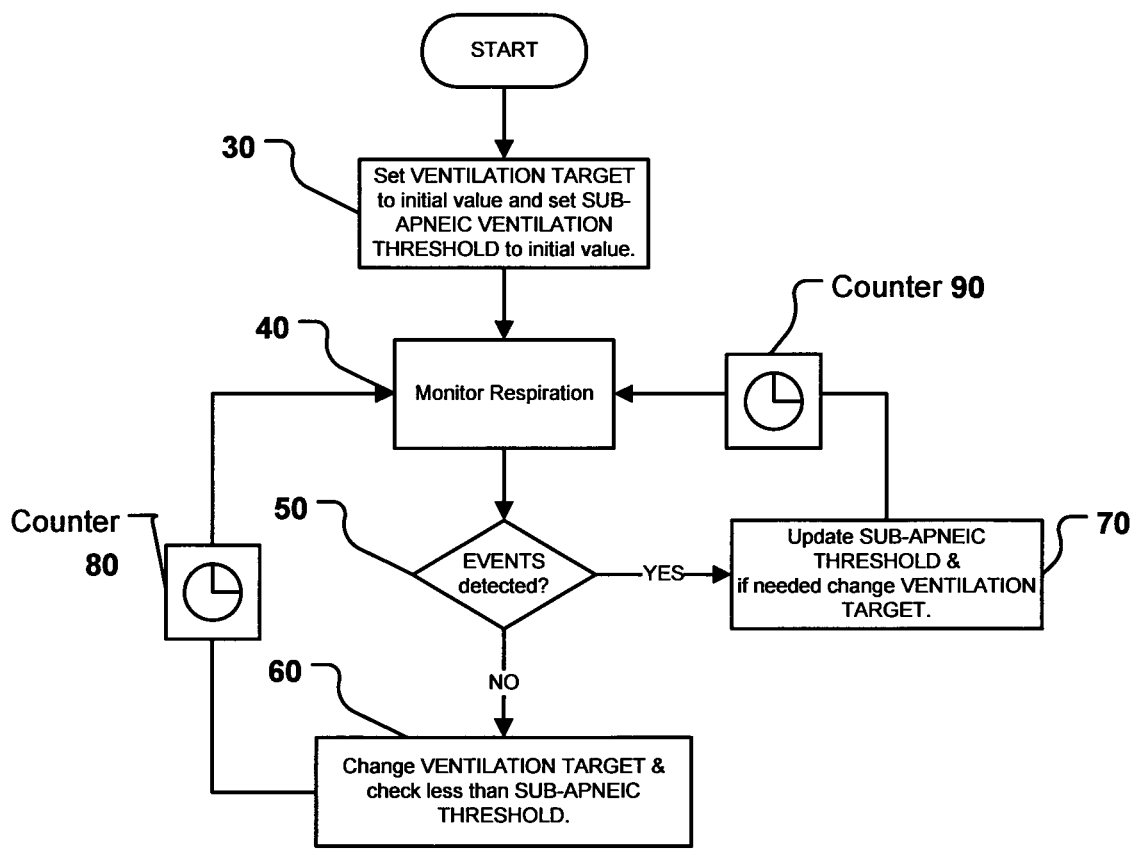
FIG. 6 illustrates an exemplary technique in accordance with certain embodiments.

An exemplary control algorithm is illustrated in FIG. 6. The exemplary control algorithm illustrated in FIG. 2, may be used with patients with or without OSA. Here in step 30, the controller or microprocessor 16 sets an initial value for the ventilation target ($V_{TARGET}$). The initial ventilation target may be determined in a number of ways as discussed herein. In addition, in step 30, the controller or microprocessor 16 sets an initial a sub-apneic ventilation threshold ($V_{SUB-APNEIC\ THRESHOLD}$). The initial value of the sub-apneic ventilation threshold may be determined in a number of ways as discussed herein. In certain embodiments, the initial value for the ventilation target ($V_{TARGET}$) and the initial sub-apneic ventilation threshold ($V_{SUB-APNEIC\ THRESHOLD}$) may also be in set in sequence as well.

In step 40, respiration is monitored for some suitable duration as discussed herein.

During the monitoring duration, the controller or microprocessor 16 analyzes data to detect events. Events may be measured, for example, as the apnea hyponea index (AHI), the hypopnea index (HI), the apnea index (AI), or combinations thereof. In step 50, if no events are detected within the monitored interval, or the number of events is less than some predetermined value (e.g., AHI<4, <5, <6, <7 or <8), then the process proceeds to step 60.

In step 60, the controller or microprocessor 16 changes to a new ventilation target that is greater than the current value of the ventilation target, and the process returns to step 40. The new ventilation target may be set in a single step, or increased incrementally over a number of breaths or period of time, so as to avoid causing arousal due to sudden changes in ventilation or pressure support levels. Additionally, if no events have been detected for a number of iterations, the sub-apneic ventilation threshold value may also be changed. In certain embodiments, the physiological apneic threshold may move up or down during different sleep stages, with disease progression, due to medication, or other reasons. In these situations a mechanism is needed for $V_{SUB-APNEIC\ THRESHOLD}$ to also increase and/or decrease. Typically, this will occur over after a number of iterations with no events. This may be implemented by adding between step 60 and 40 some type of loop counter 80, or other mechanism, that will increase the ventilation target after certain number of loops, for example, 3. Other acceptable numbers of loops may be 0, 1, 2, 3, 4, 5, 6, 7, 8, 9 or more.

The new ventilation target is also compared to the sub-apneic ventilation threshold value, to ensure that it is less than the sub-apneic ventilation threshold value.

If the new ventilation target is greater than the sub-apneic threshold ventilation value, then the ventilation target is set equal to the sub-apneic ventilation threshold value.

Referring back to step 50, if events are detected within the monitored interval, then the control algorithm proceeds to step 70.

In step 70, the sub-apneic ventilation threshold is set to the current ventilation target, minus a small margin (or buffer) and if needed a new ventilation target is set, that is different from the current ventilation target, and the process returns to step 40. In addition, the loop counter 90 resets the loop counter to zero. The value of the margin may be set in a number of ways as disclosed herein. Similarly to step 60, the new ventilation target may be set in a single step, or decreased incrementally over a number of breaths or period of time to its final value.

The sub-apneic threshold is used in step 60 to ensure that the ventilation target is not set to a value greater than the physiological apneic threshold, which may result in apnea and oscillation of the target ventilation. Typically, the sub-apneic threshold includes a margin to further mitigate the chance of oscillation, although this margin may be omitted in certain embodiments.

The methodology above, and other methodologies disclosed herein, are described with reference to particular embodiments. However, it will be readily apparent to those skilled in the art that it is possible to embody the disclosure in specific forms other than those of the embodiments described herein. For example, embodiments of the present disclosure may be combined with methods for the treatment of upper airway obstruction, for example AutoEEP or manual setting of the EPAP for the combined benefit of treating upper airway obstruction as well as minimizing sympathetic activation, and/or altering the respiratory function of a patient.

Additionally, the variable events in step 50 were described in terms of the AHI, AI or HI. However, the events could also be defined in terms of a minimum breath rate (e.g., breath rate <about 10 breaths per minute, <about 8 breaths per minute, <about 6 breaths per minute, <about 4 breaths per minute). As the ventilation target is increased and the respiratory drive diminishes, the patient's breath rate will become slower (ultimately reaching zero at apnea).

Also, the exemplary embodiments above were described in terms of a modification of the AutoVPAP. Alternatively, embodiments of the present disclosure could be implemented on an ordinary bilevel device (e.g., VPAP III). This could be accomplished by, instead of increasing or decreasing the ventilation target, increasing or decreasing the IPAP level to similar effect. Also, some autonomic benefit may be achievable if the IPAP and EPAP levels are set to the same value, i.e., if CPAP is applied. Moreover, embodiments of the present disclosure may use a bilevel variant of an OpenCPAP device. See, for example, PCT/AU2009/000671 and PCT/EP2009/002532.

Increasing the ventilation target results in increased pressure support from the AutoVPAP, which results in reduced respiratory drive, ultimately resulting in apnea as the physiological "apneic threshold" is crossed. Conversely, decreasing the ventilation target results in decreased pressure support from the AutoVPAP, which would result in increased respiratory drive.

Figure 7:
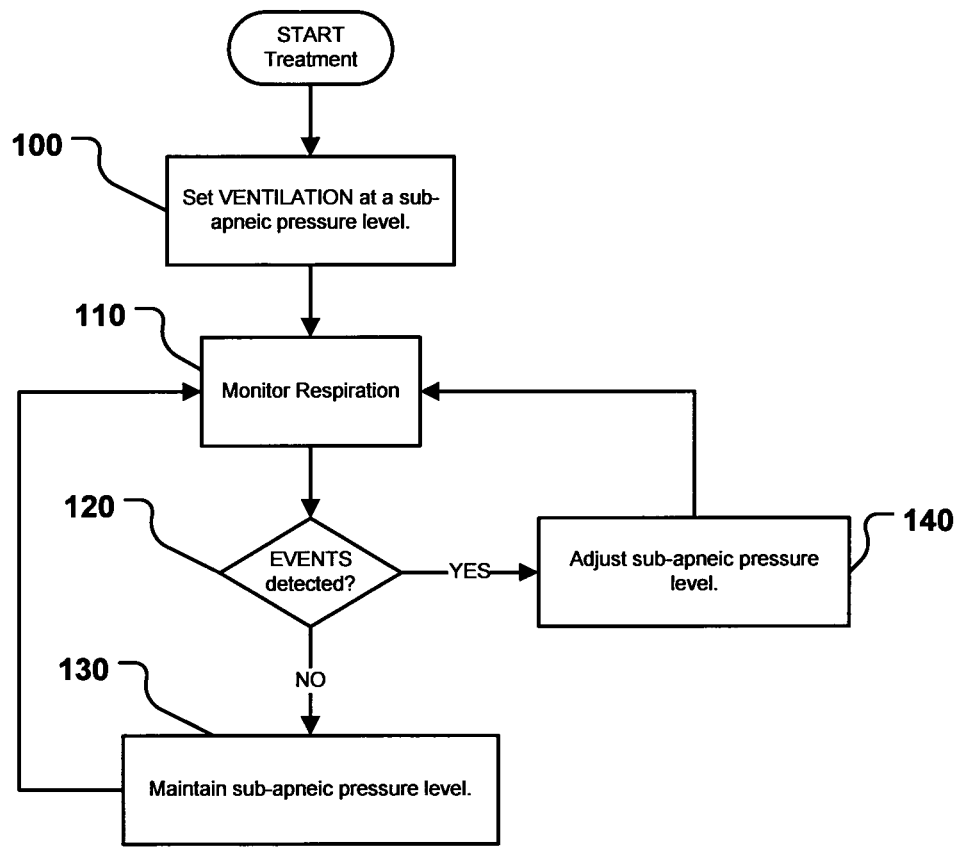
FIG. 7 illustrates an exemplary technique in accordance with certain embodiments.

In certain embodiments, treatment may proceed without an initial titration period. An exemplary control algorithm executed by the controller or microprocessor 16 operates as illustrated in FIG. 7. The exemplary control algorithm illustrated in FIG. 7, may be used with patients with or without OSA.

In step 100, the controller or microprocessor 16 sets ventilation at the desired sub-apneic pressure level. The sub-apneic pressure level may be set in a number of ways. For example, it may be: a nominal physiological value; a value calculated using a formula, e.g., based on the patient's height; a value determined from a table; a function of the patients eupneic ventilation, or a stored value from a previous treatment session or a function thereof; or a suitable combination of these techniques.

In step 110, respiration is monitored as treatment proceeds. The controller or microprocessor 16 analyzes data to detect events such as, but not limited to, the occurrence of central apneas, central hypopneas, flow limitations, or combinations thereof.

Events may be measured, for example, as the apnea hyponea index (AHI), the hypopnea index (HI), the apnea index (AI), or combinations thereof. Events may also be defined in terms of the ventilator mode, such that a switch to "timed mode" is considered an event. The sleep stage of the patient may also be monitored during monitoring step 110. In step 120 if no events are detected within the monitored interval, or the number of events is less than some predetermined value (e.g., AHI<4, <5, <6, <7 or <8), then the treatment continues to proceed, as in step 130.

In step 120, if events are detected within the monitored interval, then the control algorithm proceeds to step 140. In step 140, the sub-apneic ventilation threshold is adjusted to a different sub-apneic pressure level, and the process returns to step 110 as treatment continues to proceed. If desired, the sub-apneic pressure level may include a margin value. The margin value may be set in a number of ways; for instance it may be a predetermined fixed value or it could be calculated as a percentage of the current ventilation target. For example, the margin may be about 1%, about 2%, about 3%, about 4%, about 5%, about 6%, about 7%, about 8%, about 9% or about 10% of the current sub-apneic pressure level.

In step 140, the adjusted sub-apneic pressure level may be set in a single step, or adjusted incrementally over a number of breaths or period of time to its final value and treatment continues to proceed. In certain embodiments, the physiological apneic threshold may move up or down during different sleep stages, with disease progression, due to medication, or other reasons. In these situations the sub-apneic pressure level may also need to be adjusted by increasing, and/or decreasing the treatment pressure level.

Figure 8:
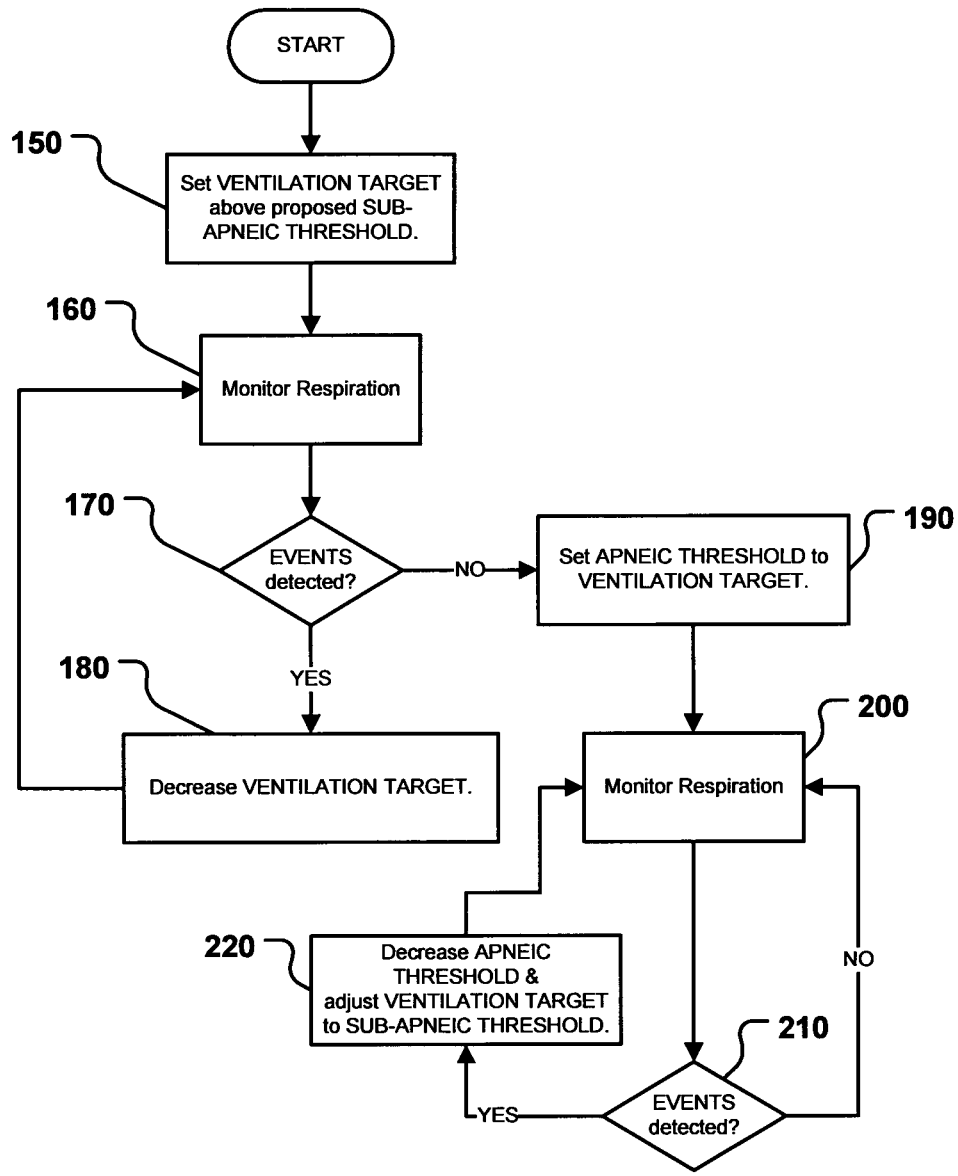
FIG. 8 illustrates an exemplary technique in accordance with certain embodiments.

In alternative embodiments, the ventilation target may be initially set at or above the sub-apneic threshold. An exemplary control algorithm executed by the controller or microprocessor 16 operates as illustrated in FIG. 8. In this embodiment the patient may initially experience respiratory events such as central apneas, central hypopneas and/or flow limitation due to reduced respiratory drive.

In step 150, the controller or microprocessor 16 sets an initial value for the ventilation target ($V_{TARGET}$) at or above the proposed sub-apneic threshold. The initial ventilation target may be determined in a number of ways as disclosed herein.

In step 160, respiration is monitored for some duration. Suitable durations are disclosed herein. During the monitoring duration, the controller or microprocessor 16 analyzes data to detect events. Events may be detected and/or measured as disclosed herein. In step 170, if no events are detected within the monitored interval, or the number of events is less than some predetermined value (e.g., AHI<4, <5, <6, <7 or <8), then the process proceeds to step 190 where the sub-apneic threshold is set to the ventilation target and then treatment continues. In step 190, the sub-apneic ventilation threshold may include a small margin (or buffer). The value of the margin may be set in a number of ways as disclosed herein.

In step 200, respiration is again monitored for some duration. Suitable durations are disclosed herein. During the monitoring duration, the controller or microprocessor 16 analyzes data to detect events. If events are detected in step 210, then the sub-apneic threshold is decreased and the ventilation target adjust to the new sub-apneic threshold in step 220 and monitoring continues in step 200, as treatment proceeds.

However, if events are detected in step 170, then in step 180, the controller or microprocessor 16, sets a new ventilation target that is less than the current value of the ventilation target, and the process returns to step 160. The process is repeated until the ventilation target has been decrease to the appropriate sub-apneic threshold. The new ventilation target may be set in a single step, or decreased incrementally over a number of breaths or period of time, so as to avoid causing arousal due to sudden changes in ventilation or pressure support levels.

Advantageously, certain embodiments of the present disclosure converge on a ventilation target at a value below the physiological apneic threshold, referred to herein as the sub-apneic threshold ventilation target. This is at or near the point of minimum respiratory drive, at which spontaneous breathing still occurs. The process or algorithm consists of the following steps:

STEP 1: initial values of the VENTILATION TARGET ($V_{TARGET}$) and the SUB-APNEIC VENTILATION THRESHOLD ($V_{SUB-APNEIC\ THRESHOLD}$) are set.

The initial VENTILATION TARGET may be determined by any of a number of means. It may be: a nominal physiological value; a value calculated using a formula, e.g., based on the patient's height; a value determined from a table; set to the patient's actual ventilation, determined by measurement or a function thereof; or a stored value from a previous treatment session or a function thereof; or combinations thereof.

The initial value of the sub-apneic ventilation threshold may be determined in a number of ways. For example, it may be: a nominal physiological value; a value calculated using a formula, e.g., based on the patient's height; a value determined from a table; a function of the patients eupneic ventilation, determined by measurement of the patients ventilation at the beginning of the session or a function thereof; or a stored value from a previous treatment session or a function thereof; or a suitable combination of these techniques. In certain embodiments, the initial value for the ventilation target ($V_{TARGET}$) and the initial a sub-apneic ventilation threshold ($V_{SUB-APNEIC\ THRESHOLD}$) do not have to be set at the same time. They may be set in sequence as well.

STEP 2: respiration is monitored for some duration.

A suitable duration might be 20 minutes, but shorter or longer durations may be used. Other suitable durations might be, for example, 5 minutes, 10 minutes, 20 minutes, 30 minutes or 40 minutes.

STEP 3 (a): if no EVENTS are detected within the monitored interval or the number of EVENTS is less than some predetermined value (e.g. AHI<4, <5, <6, <7 or <8), then the process proceeds to STEP 4.

EVENTS may be measure as the apnea hyponea index (AHI), the hypopnea index (HI) or the apnea index (AI). Methods for apnea and hypopnea detection are established and known to someone familiar with the art.

STEP 4: a new VENTILATION TARGET is set, greater than the current value of the VENTILATION TARGET, and the process returns to STEP 2.

The new VENTILATION TARGET may be set in a single step, or increased incrementally over a number of breaths or period of time, so as to avoid causing arousal due to sudden changes in ventilation or pressure support levels.

If an SUB-APNEIC THRESHOLD (see STEP 5) has been stored, the new VENTILATION TARGET may also be compared to the SUB-APNEIC THRESHOLD, to ensure that it is less than the physiological apneic threshold.

If the new VENTILATION TARGET is greater than the SUB-APNEIC THRESHOLD, then the VENTILATION TARGET is set equal to the SUB-APNEIC THRESHOLD.

STEP 3 (b): alternatively if EVENTS are detected within the monitored interval, then the process proceeds to STEP 5.

STEP 5: the current VENTILATION TARGET, minus a small MARGIN (or buffer), is stored as the SUB-APNEIC THRESHOLD and a new VENTILATION TARGET is set, less than the current ventilation target, and the process returns to STEP 2.

The MARGIN may be set in a number of ways; for instance it may be a predetermined fixed value or it could be calculated as a percentage of the current VENTILATION TARGET. For example, the margin may be about 1%, about 2%, about 3%, about 4%, about 5%, about 6%, about 7%, about 8%, about 9% or about 10% of the current ventilation target. The MARGIN may be set to zero.

Similarly to STEP 4, the new VENTILATION TARGET may be set in a single step, or decreased incrementally over a number of breaths or period of time to its final value.

In certain embodiments, you want the VENTILATION TARGET to eventually converge on a value just below the physiological apneic threshold. In certain embodiments, this is (or close to) the point of minimum respiratory drive, at which spontaneous breathing still occurs.

The SUB-APNEIC VENTILATION THRESHOLD is used in STEP 4 to ensure that the VENTILATION TARGET is not set to a value greater than the physiological apneic threshold which may lead to oscillation of the VENTILATION TARGET, as it crosses the physiological apneic threshold and is reset. Typically the SUB-APNEIC VENTILATION THRESHOLD is less than the physiological apneic threshold by the amount of the MARGIN to further mitigate the chance of oscillation. Although this margin may be omitted in certain applications if desired.

In certain embodiments, the VENTILATION TARGET and SUB-APNEIC VENTILATION THRESHOLD may be adapted on a continuous basis using the algorithm. Alternatively, in certain embodiments the therapy may be divided into titration and treatment periods, in which case the above process is applied during the titration phase to determine the SUB-APNEIC VENTILATION THRESHOLD. In the treatment phase, the VENTILATION TARGET is fixed and set to the titrated SUB-APNEIC VENTILATION THRESHOLD value.

The disclosed devices, systems, processor-readable media, and methods for inhibiting and/or reducing sympathetic activation through control, and/or alteration of respiratory function may be used in for treating patients without upper airway obstructions and/or obstructive sleep apnea (OSA).

The disclosed devices, systems, processor-readable media, and methods for inhibiting and/or reducing sympathetic activation through control, and/or alteration of respiratory function may be combined with methods for the treatment of upper airway obstruction, for example, but not limited to, AutoEEP or manual setting of the EPAP, for the combined benefit of treating upper airway obstruction and/or modifying, inhibiting and/or reducing sympathetic activation.

In certain embodiments, the variable EVENTS in STEP 3 are defined in terms of the AHI, AI, HI, or combinations thereof. Alternatively, it could be defined in terms of a minimum breath rate (e.g. BREATH RATE <10 breaths per minute). As the VENTILATION TARGET is increased and the respiratory drive diminishes, the patient's breath rate will become slower (ultimately reaching zero at apnea). In certain embodiments, the minimum breath rate could be defined as 4, 5, 6, 7, 8, 9, 10, 12, 13, 14 or 15 breaths per minute. In certain embodiments, the minimum breath rate could be defined as <4, <5, <6, <7, <8, <9, <10, <12, <13, <14 or <15 breaths per minute.

In certain embodiments, the method is implemented as a modification of the AutoVPAP. Alternatively, the method could be implemented on an ordinary bilevel device (e.g. VPAP III). Instead of increasing or decreasing the VENTILATION TARGET, the IPAP level would be increased or decreased, to similar effect.

In the above scenario, in certain embodiments some autonomic benefit may be achieved if the IPAP and EPAP levels are set to the same value, i.e., if CPAP is applied. For example, if Type II diabetics, who may or may not have OSA, are placed on a CPAP device at a fixed pressure of 8 cm of $H_2O$. Other fixed pressures may be used for the treatment, for example 4, 5, 6, 7, 9, 10, 11, 12, 13, 14, 15 or 16 cm of $H_2O$.

An alternative to using an NIV device may be to use a bilevel variant of the OpenCPAP device.

The exemplary approaches described, may be carried out using suitable combinations of software, firmware and hardware and are not limited to particular combinations of such. Computer program instructions for implementing the exemplary approaches described herein may be embodied on a processor-readable storage medium, such as a magnetic disk or other magnetic memory, an optical disk (e.g., DVD) or other optical memory, RAM, ROM, or any other suitable memory such as Flash memory, memory cards, etc. The embodiments are merely illustrative and should not be considered restrictive. The scope of the disclosure is given by the appended claims and all variations and equivalents which fall within the range of the claims are intended to be embraced therein.

What is claimed is:

1. A method for determining a sub-apneic ventilation target for a ventilator comprising the steps of:
   setting a ventilation target to an initial value;
   monitoring a patient's respiration for a duration;
   analyzing data representing the patient's respiration to detect events indicating an apneic threshold;
   if no events are detected, increasing the ventilation target and continue to monitor the patient's respiration for a duration;
   if events are detected, setting a sub-apneic threshold and reducing the ventilation target to substantially the sub-apneic threshold or lower to determine the sub-apneic ventilation target;
   wherein the determined sub-apneic ventilation target is such that chronic sympathetic activation of the patient is mitigated when ventilation is provided at substantially the determined sub-apneic ventilation target.

2. A method of claim 1, wherein the sub-apneic threshold is initially set at an initial value and is subsequently reset based on the detected events to an updated sub-apneaic threshold.

3. The method of claim 2, wherein the updated sub-apneic threshold is used to treat the patient.

4. The method of claim 1, wherein the determined sub-apneic ventilation target is used to treat the patient.

5. The method of claim 1, wherein the determined sub-apneic ventilation target is less than the sub-apneic threshold by an additional margin and is use to treat the patient.

6. The method of claim 1, wherein the ventilation is substantially maintained at the determined sub-apneic ventilation target.

7. The method of claim 1, wherein the determined sub-apneic ventilation target is adjusted as needed over time to be substantially at the sub-apneic threshold or lower.

8. The method of claim 1, wherein the sub-apneic threshold will vary over time and the chronic sympathetic activation of the patient is substantially continuously mitigated by increasing or decreasing the sub-apneic ventilation target as needed over time.

9. The method of claim 1, wherein the method is computer implemented.

10. The method of claim 1, wherein the events are detected using an apnea hypopnea index.

11. The method of claim 1, wherein the events are detected when a hypopnea index is above a threshold.

12. The method of claim 1, wherein the events are detected when an apnea index is above a threshold.

13. The method of claim 1, wherein the events are detected when a patient's breath rate is below a threshold.

14. The method of claim 1, wherein the events are detected when the ventilator mode switches to a timed mode.

15. The method of claim 1, wherein the events are detected when an apnea hypopnea index is above a threshold a predetermined number of times.

16. The method of claim 1, wherein the events are detected when a hypopnea index is above a threshold a predetermined number of times.

17. The method of claim 1, wherein the events are detected when an apnea index is above a threshold a predetermined number of times.

18. The method of claim 1, wherein the events are detected when the patient's breath rate is below a threshold a predetermined number of times.

19. A method of treating a patient for chronic sympathetic activation by setting a sub-apneic ventilation target of a ventilator in accordance with claim 1.

20. The method of claim 19, wherein the patient is asleep.

21. The method of claim 19, wherein the patient is awake.

22. The method of claim 1, wherein the ventilator is a bilevel ventilator.

23. A method of treating a patient for one or more of the conditions selected from the group consisting of hypertension, Type II diabetes, obesity, metabolic syndrome, and congestive heart failure, by setting a sub-apneic ventilation target of a ventilator in accordance with claim 1.

24. The method of claim 1, wherein the initial value for the ventilation target or the sub-apneic ventilation threshold is set to one or more values selected from the group consisting of a nominal physiological value, a value calculated using a formula; a value determined from a table; the patient's respiration value, and a stored value from a previous treatment session.

25. A processor-readable medium having instructions therein that, when executed, cause a processor to control a ventilator to treat a patient for chronic sympathetic activation by setting a sub-apneic ventilation target of the ventilator in accordance with the method of claim 1.

26. The processor-readable medium of claim 25, wherein the patient is asleep.

27. The processor-readable medium of claim 25, wherein the patient is awake.

28. The processor-readable medium of claim 25, wherein the ventilator is a bilevel ventilator.

29. A processor-readable medium having instructions therein that, when executed, cause a processor to control a ventilator to treat a patient for one or more of the conditions selected from the group consisting of hypertension, Type II diabetes, obesity, metabolic syndrome, and congestive heart failure, by setting a sub-apneic ventilation target of the ventilator in accordance with the method of claim 1.

30. A device for treating a patient for chronic sympathetic activation by setting a sub-apneic ventilation target of a ventilator in accordance with the method of claim.

31. A device for treating a patient for one or more of the conditions selected from the group consisting of hypertension, Type II diabetes, obesity, metabolic syndrome, and congestive heart failure, by setting a sub-apneic ventilation target of a ventilator in accordance with the method of claim 1.

32. The method of claim 1, wherein the patient is not being treated for OSA.

33. The method of claim 1, wherein the patient is also being treated for OSA.

34. The method of claim 1, wherein the patient does not have OSA.

35. The method of claim 1, wherein the patient does have OSA.

36. A processor-readable medium having instructions therein that, when executed, cause a processor to perform the steps of:
    setting a ventilation target to an initial value;
    monitoring a patient's respiration for a duration;
    analyzing data representing the patient's respiration to detect events indicating an apneic threshold;
    if no events are detected, increasing the ventilation target and continuing to monitor the patient's respiration;
    if events are detected, setting a sub-apneic threshold and reducing the ventilation target to substantially the sub-apneic threshold or lower to determine a sub-apneic ventilation target;
    wherein the sub-apneic ventilation target is such that chronic sympathetic activation of the patient is mitigated when ventilation is provided at substantially the sub-apneic ventilation target.

37. The processor-readable medium of claim 36, wherein the events are detected when an apnea hypopnea index is above a threshold.

38. The processor-readable medium d of claim 36, wherein the events are detected when a hypopnea index is above a threshold.

39. The processor-readable medium of claim 36, wherein the events are detected when an apnea index is above a threshold.

40. The processor-readable medium of claim 36, wherein the events are detected when the patient's breath rate is below a threshold.

41. The processor-readable medium of claim 36, wherein the events are detected when an apnea hypopnea index is above a threshold a predetermined number of times.

42. The processor-readable medium of claim 36, wherein the events are detected when a hypopnea index is above a threshold a predetermined number of times.

43. The processor-readable medium of claim 36, wherein the events are detected when an apnea index is above a threshold a predetermined number of times.

44. The processor-readable medium of claim 36, wherein the events are detected when a patient's breath rate is below a threshold a predetermined number of times.

45. The processor-readable medium of claim 36, wherein the initial value is set to one or more values selected from the group consisting of a nominal physiological value, a value calculated using a formula; a value determined from a table; the patient's respiration value, and a stored value from a previous treatment session.

46. The processor-readable medium of claim 36, wherein patient is not being treated for OSA.

47. The processor-readable medium of claim 36, wherein the patient is also being treated for OSA.

48. The processor-readable medium of claim 36, wherein the patient does not have OSA.

49. The processor-readable medium of claim 36, wherein the patient does have OSA.

50. A device for determining a sub-apneic ventilation target for a ventilator comprising:
    a blower in air communication with a mask worn by a patient;
    a respiratory monitor;
    a processor in communication with the respiratory monitor and the blower, wherein the processor controls the operation of the blower; and
    a memory connected to the processor, wherein the memory has instructions therein that cause the processor to perform the steps of,
    setting a ventilation target to an initial value;
    monitoring the patient's respiration for a duration;
    analyzing data representing the patient's respiration to detect events indicating an apneic threshold;
    if no events are detected, increasing the ventilation target;
    if events are detected, setting a sub-apneic threshold and reducing the ventilation target to substantially the sub-apneic threshold or lower to determine the sub-apneic ventilation target;
    wherein the sub-apneic ventilation target is such that chronic sympathetic activation of the patient is mitigated when ventilation is provided at the sub-apneic ventilation target.

51. The device of claim 50, wherein the events are detected when an apnea hypopnea index is above a threshold.

52. The device of claim 50, wherein the events are detected when a hypopnea index is above a threshold.

53. The device of claim 50, wherein the events are detected when an apnea index is above a threshold.

54. The device of claim 50, wherein the events are detected when the patient's breath rate is below a threshold.

55. The device of claim 50, wherein the events are detected when an apnea hypopnea index is above a threshold a predetermined number of times.

56. The device of claim 50, wherein the events are detected when a hypopnea index is above a threshold a predetermined number of times.

57. The device of claim 50, wherein the events are detected when an apnea index is above a threshold a predetermined number of times.

58. The device of claim 50, wherein the events are detected when a patient's breath rate is below a threshold a predetermined number of times.

59. The device of claim 50, wherein the patient is asleep.

60. The device of claim 50, wherein the patient is awake.

61. The device of claim 50, wherein the ventilator is a bilevel ventilator.

62. The device of claim 50, wherein the initial value is set to one or more values selected from the group consisting of a nominal physiological value, a value calculated using a formula; a value determined from a table; the patient's respiration value, and a stored value from a previous treatment session.

63. The device of claim 50, wherein the patient is not being treated for OSA.

64. The device of claim 50, wherein the patient is also being treated for OSA.

65. The device of claim 50, wherein the patient does not have OSA.

66. The device of claim 50, wherein the patient does have OSA.

* * * * *